United States Patent [19]

Hector

[11] Patent Number: 4,851,389
[45] Date of Patent: Jul. 25, 1989

[54] USE OF NIKKOMYCIN COMPOUNDS TO TREAT INFECTIONS OF DIMORPHIC, HIGHLY CHITINOUS FUNGI

[75] Inventor: Richard F. Hector, Dublin, Calif.

[73] Assignee: Miles Laboratories, Inc., Elkhart, Ind.

[21] Appl. No.: 75,793

[22] Filed: Jul. 20, 1987

Related U.S. Application Data

[63] Continuation-in-part of Ser. No. 29,917, Mar. 25, 1987, abandoned.

[51] Int. Cl.$^4$ .................. A61K 31/71; A61K 31/70
[52] U.S. Cl. .................................. 514/43; 514/23; 536/23; 536/24
[58] Field of Search ............. 536/23, 24; 514/43, 514/23

[56] References Cited

U.S. PATENT DOCUMENTS

| | | | |
|---|---|---|---|
| 4,046,881 | 9/1977 | Dähn et al. | 536/23 |
| 4,158,608 | 6/1979 | Dähn et al. | 536/24 |
| 4,287,186 | 9/1981 | Zähner et al. | 536/24 |
| 4,315,922 | 2/1982 | Hagenmaier et al. | 536/23 |
| 4,402,947 | 9/1983 | Moeschler et al. | 536/24 |
| 4,552,954 | 11/1985 | Moeschler et al. | 536/24 |
| 4,585,761 | 4/1986 | Zähner et al. | 536/23 |

OTHER PUBLICATIONS

Müller et al; Arch. Microbiol. 130:195–198 (1981).
Hector et al; Antimicrobial Agents and Chemotherapy, 29(3):389–394, Mar. 1986.
Brillinger; Arch. Microbiol. 121:71–74 (1979).
McMurrough et al; J. Biol. Chem. 246(12):3999–4007 (1971).
Becker et al; Antimicrobial Agents and Chemotherapy, 23(6):926–929 (1983).

*Primary Examiner*—Ronald W. Griffin
*Assistant Examiner*—Nancy S. Carson
*Attorney, Agent, or Firm*—James A. Giblin

[57] ABSTRACT

Method of treating an infection of dimorphic, highly chitinous fungi, the method comprising administering therapeutically effective amounts of a nikkomycin or derivative thereof. Treatment is especially suited for infections of medically significant fungi having cell walls with about 10–20% by weight chitin in the parasitic phase. Such fungi include *Coccidiodes immitis, Histoplasma capsulatum, Blastomyces dermatitidis,* and *Paracoccidiodes brasiliensis.*

7 Claims, No Drawings

USE OF NIKKOMYCIN COMPOUNDS TO TREAT INFECTIONS OF DIMORPHIC, HIGHLY CHITINOUS FUNGI

This is a continuation-in-part of Ser. No. 06/029,917 filed on Mar. 25, 1987, now abandoned.

BACKGROUND OF THE INVENTION

1. Field

This disclosure is concerned generally with the use of antibiotics to treat infections of medically significant fungi. Specifically, the disclosure is concerned with the use of a class of antibiotics known as nikkomycins to treat infections of dimorphic and highly chitinous (more than 10% by weight chitin) fungi in mammals.

2. Prior Art

Compounds inhibitory to the synthesis of fungal cell wall material (synthase inhibitors) have been reported recently to have demonstrable effects against fungi of agricultural importance (U.S. Pat. Nos. 4,315,922 and 4,158,608). See also U.S. Pat. Nos. 4,585,761 and 4,552,954 for descriptions of the preparation and purification of such compounds. The agents mentioned in the cited patents, nikkomycins, together with similar agents known as polyoxins, are known to act by interfering with the synthesis of chitin in the cell walls of fungi. Because fungi of medical importance to humans also have varying amounts of chitin in their cell walls, experiments have been conducted to determine if the chitin synthase inhibitors are capable of inhibiting the growth of such fungi (Hector and Pappagianis, J. Bacteriol. 154:488-498, 1983, and Hector and Braun, Antimicrobial Agents Chemother, 29:389-394, 1986). In earlier work, certain fungi such as Candida albicans were reported to be insensitive to chitin synthase inhibitors (see Naider et al, Antimicrobial Agents Chemother. 24:787-796, 1983). Subsequently, C. albicans was found to be more sensitive to nikkomycins than polyoxins (see Yadan et al, J. Bacteriol. 160:884-888, 1984) but the concentrations necessary for killing that yeast would (for toxicity reasons) preclude their use as chemotherapeutic agents for yeast infections (see Hector and Braun, Antimicrobial Agents Chemother., 29:389-394, 1986).

Quite surprisingly, I have now found that nikkomycin compounds are efficacious in treating fungal infections if the fungal agents are highly chitinous in the parasitic phase. Although the results described below were surprising, it is thought that they may be based on the difference in chitin content in the cell walls of the fungi (see, for example, Chattaway et al, J. Gen. Microbiol. 51:367-376, 1967, where C. albicans is reported to contain less than 1% by weight chitin in the cell wall).

As reported below, data from in vivo and in vitro studies using Coccidioides immitis dimorphic fungi show that nikkomycin compounds are efficacious in treating infections of such fungi.

SUMMARY OF INVENTION

Nikkomycin compounds have been found effective in treating a mammal having an infection of a dimorphic, highly chitinous fungus. The compounds are especially suited for treating medically significant fungi having cell walls comprising at least 10% by weight chitin in the parasitic phase. Such fungi include Coccidioides immitis, Histoplasma capsulatum, Blastomyces dermatitides, and Paracoccidioides brasiliensis. In one embodiment the nikkomycin is nikkomycin X or nikkomycin Z administered in an amount sufficient to treat infection of the dimorphic, highly chitinous fungi in a mammal (such as the mouse). In another embodiment, the amount of nikkomycin or a derivative thereof is sufficient to inhibit the enzyme chitin synthase. It is thought that the treatment with nikkomycin will be especially useful against C. immitis infections, the causative agent of what is commonly referred to as valley fever. As used herein, the term highly chitinous means that the chitin must be at least 10% by weight of the cell wall of the organism. The term dimorphic means having two distinct growth phases (i.e. saprophytic and parasitic phases). Therapeutically effective amount (of nikkomycin or a nikkomycin derivative) means an amount (commonly expressed as mg/kg body weight) sufficient to result in clinical improvement in the signs and symptoms of disease and/or prevention of mortality in the more critically ill.

Pharmaceutically acceptable vehicle means a carrier suitable for delivering safe and efficacious amounts of the nikkomycin or a derivative thereof.

As can be appreciated, the above microorganisms are known as primary pulmonary pathogens (cf. opportunistic pathogens) and it is thought that the nikkomycin compounds are especially useful in treating infections of that class of pathogens.

SPECIFIC EMBODIMENTS

Strains and conditions of culture. Coccidioides immitis strain Silveira was employed in illustrative studies. For growth of arthrospores, slants of glucose-yeast extract agar were inoculated with an endospore suspension and allowed to grow for several weeks at room temperature. The arthrospores were collected by gently disrupting the mycelial growth under liquid, the liquid decanted, centrifuged, ad the pellet washed and resuspended. The spherule phase of the fungus was maintained by repeated passage of endospores in liquid modified Converse medium (Trans. N.Y. Acad. Sci. 20:436-449, 1960) incubated at 37° C. with shaking.

In vitro experiments.

Susceptibility testing was performed by subjecting suspensions of 15 h immature spherules (final O.D. of 0.2 at 440 nm) to concentrations of either nikkomycin X or nikkomycin Z of 0.04, 0.1, or 0.4 mM (final concentration diluted in modified Converse medium) with continued incubation for intervals of 8 and 24 h. Inhibition of growth was to be determined visually by light microscopy and by staining with calcofluor white, a fluorchrome with known affinity for chitin, followed by epifluorescent microscopy.

In vivo studies.

A murine model of coccidioidomycosis was used to assess the compounds in vivo. Outbred Swiss-Webster mice, 25 g. average weight, were anesthetized, then inected intranasally by placing 0.05 ml of a suspension containing 500 arthrospores of C. immitis on the nares of each animal, and allowing them to inhale the suspension. A total of 30 animals were infected, then divided into groups of 10 each for testing. The following day therapy was begun. Nikkomycin X and Z were prepared by suspending the powders in sterile water to achieve a dose of 100 mg/kg body weight delivered in 0.1 ml. The liquids were aliquoted into 1 ml portions and held at −70° C. until needed. Animals were treated with nikkomycin X, nikkomycin Z, or given sterile water starting the day after infection. Doses were given orally three times a day for a total of nine days. Nine days after the cessation of therapy, 5-6 animals from each of the three groups were sacrificed and their lungs, livers, and spleens removed for quantitative cultures for the enumeration of viable fungus. Organ homogenates were cultured on Sabourauds agar and held for two weeks before being considered negative.

Results

In vitro studies.

Examination of cultures at the 8 h interval revealed that the two highest concentrations of nikkomycin X (NX) and nikkomycin Z (NZ) resulted in the complete cessation of growth of the fungus. In general, only small spherules with no evidence of endosporulation were present. At the lowest concentration, it was evident that endosporulation had been arrested by both nikkomycin X and Z, but a small percentage of swollen cells, indicating osmotic sensitivity and a weakened cell wall, were seen with both compounds. In general, NZ appeared slightly more effective than NX. In contrast, the control culture showed normal patterns of maturation, i.e., endosporulation followed by the rupture of the spherule to release the progeny endospores. Results of epifluorescent microscopy confirmed the absence of cleavage planes and indicated a reduction of chitin content in the cell walls.

In vivo studies.

Results of the cultures demonstrated that the control animals were heavily infected, with 5.766 log10 colony forming units of fungus in lungs, 2.256 log10 units in the livers, and 1.594 log10 units in the spleens as average values for 6 sacrificed animals. In marked contrast, none of the cultures from treated animals were positive for fungus, indicating a complete sterilization of the organs by the nikkomycins. These results are summarized in the Table below.

TABLE

Use of Nikkomycin X and Z in Murine Coccidioidomycosis*

| Group** | Geometric Mean Log CFU/GM Tissue | | |
|---|---|---|---|
| | Lung | Liver | Spleen |
| Control | 5.766 | 2.256 | 1.594 |
| Nikkomycin X | Neg | Neg | Neg |
| Nikkomycin Z | Neg | Neg | Neg |

*5-6 Animals/group infected intranasally with 500 arthrospores of *C. Immitis*.
**Animals given 100 mg/kg nikkomycin orally T.I.D. starting 18 hours after infection; controls received water.

The findings of the in vivo experiments in which treated animals were devoid of viable fungus while the control animals were heavily infected in the lungs with evidence of dissemination were unexpected. As has been previously reported (Yadan et al, J. Bacteriol. 160:884-888, 1984) the portal of entry for the nikkomycins into the fungal cells is via the peptide transport system. Given that in an animal host the infecting fungus (in the organs or bloodstream) is constantly bathed in a millieu rich in peptides, it was reasonable to assume that competition for available transport sites could have significantly reduced the amount of active substance transported into the cell, thus reducing efficacy of the drugs. This situation would not manifest itself in agricultural applications of the nikkomycins because most phytopathic fungi and insects exist as ectoparasites. Thus, the findings reported herein represent a unique and unexpected application.

Discussion

The data indicate that nikkomycins X and Z can serve as efficacious agents against dimorphic, highly chitinous fungi such as C. immitis. The compounds appear to work by interfering with normal cell wall synthesis, a necessary component of endosporulation in the fungus. The animal experiment indicated that animals infected with a potentially lethal challenge with C. immitis can be protected by administration of the compounds orally for as short a period as 9 days. Therefore, it is thought that these agents should be considered as antifungal drugs in human use for the described fungus as well as other medically important fungi in which chitin can be demonstrated to be present in the cell wall in relatively high amounts (i.e. more than 10% by weight or in the range of 10–20% by weight).

FURTHER EXAMPLES

The previous in vivo experiments demonstrated the ability of orally administered doses of nikkomycin X and Z to sterilize the organs of mice infected with a potentially, though not acutely, lethal number of arthrocondia of *Coccidioides immitis* via the pulmonary route. Two additional experiments were done; one to test of ability of these two compounds to prolong survival in animals infected with a more lethal challenge of this fungus, and a second to assess the pathology of lungs from mice infected with a massive challenge and treated on a short-term basis with nikkomycin X or Z.

Materials and Methods

Survival Experiment: Female Swiss-Webster mice (Charles River Labs.), 25 grams average weight, were anesthetized and then infected via the intranasal route with 4800 arthrocondia of *C. immitis* strain Silveira. Fifty-two hours after infection, groups of 9–10 animals animals each were begun on a 9 day B.I.D. regimen of 75 mg/kg of nikkomycin X or Z delivered orally, with two groups of mice held without treatment. Upon the first death in one of the untreated groups, the remaining survivors of that group were initiated on an oral regimen of nikkomycin X, given T.I.D. at 75 mg/kg for a total of 9 days. Additionally, because of the low mortalities seen in the two initial treatment groups, five animals each from the nikkomycin X and Z groups were sacrificed and autopsied. Four animals were processed for organ cultures of lungs, livers, and spleens, and the lungs from the fifth animals were processed for histological examination. The remaining animals were held for observation for a total of 30 days, then survivors posted for organ cultures.

Pathology Studies: Six female Swiss-Webster mice were infected intranasally with 10,000 arthrocondida of *C. immitis* silveira. After a delay of 52 hours, two mice each were begun on an oral regimen of nikkomycin X or Z at 75 mg/kg given B.I.D. for 4 days, with two mice held as controls. The day following cessation of treatment, all mice were sacrificed, and lungs, livers, and kidneys were removed for histology.

Results: Deaths in the control group had rapid, onset, reaching 80% mortality by day 11. Therapy with nikkomycin Z was completely successful in preventing death, while there was a single death in animals receiving nikkomycin X in the initial group. In those animals given nikkomycin X after the first death there were 4 survivors, indicating therapy with this compound was effective in reducing death in moribund animals, with a survival rate of 50% (4/8) in animals receiving therapy. Data from the organ cultures taken at days 18 and 30, shows that both compounds are able to greatly reduce the amount of viable fungus in the lungs and prevent the dissemination of the disease to two key organs of the reticuloendothelial system.

Histology: Examination of the lung histological preparations from the treated mice of the survival experiment failed to reveal any recognizable fungal elements or evidence of significant pathology. In the experiment conducted exclusively for the purposes of histology, the lung preparation from control animals showed large numbers of parasitic phase *C. immitis* and pathology consistent with early inflammatory disease and granuloma formation described for coccidioidomyciosis. In marked contrast, lung preparations from nikkomycin Z-treated mice showed no evidence of fungus and only limited pathology (i.e., infrequent foci of inflammation). Examination of the nikkomycin X lung preparations showed no evidence of intact fungal cells, though there existed less than 10 cells per slide with an abberant morphology which could have been fungal in origin.

Summary: Data indicates that orally administered nikkomycins X and Z are markedly effective in preventing mortality and morbidity in the described animal model of pulmonary coccidioidomuyciosis. In marked contrast to previous reports of drugs effective in reducing disease in this model, the duration of therapy was short, yet the results are superior. Also in contrast to other human use antifungal agents of record, the nikkomycin X and Z appear to be potentially fungicidal, as demonstrated by the lack of microscopic evidence of intact fungi in the histologic preparations from treated animals. As such, this confirms and extends the findings documented in the earlier examples.

Given the above disclosure, it is thought variations (such as ideal dosages, vehicles, etc.) will occur to those skilled in the art. For example, it is thought that the nikkomycins may also be effective against infections in mammals by chitinous organisms other than the dimorphic fungi of this disclosure. One such organism is the parasite *Pneumocystis carinii* which causes pneumonia in certain immuno-compromised individuals.

Accordingly, it is intended that the above examples should be limited only by the following claims.

I claim:

1. A method of treating a mammal infected with a dimorphic, highly chitinous fingi which are primary poulmonary pathogens, the method comprising adminstering to the mammal therapeuticlly efective amounts of nikkomycin X or nikkomycin Z.

2. The method of claim 1 wherein the fungi have cell walls comprising at least about 10% by weight chitin.

3. The method of claim 2 wherein the cell walls comprise about 10–20% by weight chitin.

4. The method of claim 1 wherein the nikkomycin is administered in a pharmaceutically acceptable vehicle.

5. The method of claim 4 wherein the nikkomycin is administered orally.

6. The method of claim 1 wherein the fungi are selected from the group consisting of *Coccidioides immitis, Histoplasma capsulatum, Blastomyces dermatitides,* and *Paracoccidioides brasiliensis.*

7. The method of claim 6 wherein the fungi are *Coccidioides immitis.*

* * * * *

UNITED STATES PATENT AND TRADEMARK OFFICE
CERTIFICATE OF CORRECTION

PATENT NO. : 4,851,389

DATED : July 25, 1989

INVENTOR(S) : Richard F. Hector

It is certified that error appears in the above-identified patent and that said Letters Patent is hereby corrected as shown below:

Claim 1, line 2: fingi should be fungi

Claim 1, line 3: poulmonary should be pulmonary

Signed and Sealed this

Fifteenth Day of May, 1990

Attest:

HARRY F. MANBECK, JR.

*Attesting Officer*  *Commissioner of Patents and Trademarks*